US006323014B1

(12) United States Patent
Breel et al.

(10) Patent No.: US 6,323,014 B1
(45) Date of Patent: Nov. 27, 2001

(54) METHOD AND COMPOSITION FOR ENHANCING THE ACTIVITY OF AN ENZYME

(75) Inventors: Greta Johanna Breel; Daniel Convents; Willem Van Liemt; Ton Swarthoff; Robin Stefan Twisker, all of Vlaardingen (NL)

(73) Assignee: Unilever Home & Personal Care division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/596,998

(22) Filed: Jun. 20, 2000

(30) Foreign Application Priority Data

Jun. 23, 1999 (EP) ........................................ 99202023

(51) Int. Cl.[7] ........................................ C12N 9/96

(52) U.S. Cl. ........................ 435/188; 81/102; 81/107; 81/111; 81/137; 81/401; 252/8.91; 252/99; 252/102; 252/186.38; 252/186.39; 252/186.43; 510/300; 510/303; 510/305; 510/312; 510/315; 510/320; 510/350; 510/351; 510/356; 510/367; 510/369; 510/374; 510/375; 510/376; 510/377; 510/392; 510/393; 510/502; 510/530

(58) Field of Search ........................ 81/102, 107, 111, 81/137, 401; 252/8.91, 99, 102, 186.38, 186.39, 186.43; 510/300, 303, 305, 312, 315, 320, 350, 351, 356, 367, 369, 374–377, 392–393, 502, 530; 435/188

(56) References Cited

U.S. PATENT DOCUMENTS

| | | | | |
|---|---|---|---|---|
| 4,690,895 | | 9/1987 | Farrell | 435/278 |
| 5,700,771 | * | 12/1997 | Hardy et al. | 510/315 |
| 5,752,980 | * | 12/1998 | Pedersen et al. | 8/111 |
| 5,912,405 | | 6/1999 | Schneider et al. | 8/111 |
| 5,965,510 | | 10/1999 | Schneider et al. | 510/397 |
| 6,107,264 | * | 8/2000 | van Der Helm et al. | 510/320 |

FOREIGN PATENT DOCUMENTS

| | | |
|---|---|---|
| 424 398 | 5/1991 | (EP) . |
| 0 453 003 | 10/1991 | (EP) . |
| 91/05839 | 5/1991 | (WO) . |
| 94/12619 | 6/1994 | (WO) . |
| 94/12620 | 6/1994 | (WO) . |
| 94/12621 | 6/1994 | (WO) . |
| 96/12845 | 5/1996 | (WO) . |
| 97/06244 | 2/1997 | (WO) . |
| 97/11217 | 3/1997 | (WO) . |

OTHER PUBLICATIONS

PCT International Search Report in a PCT application PCT/EP 00/05233.

European Search Report in a European Application 99 20 2023.

* cited by examiner

*Primary Examiner*—Francisco Prats
*Assistant Examiner*—K. C. Srivastava
(74) *Attorney, Agent, or Firm*—Rimma Mitelman

(57) ABSTRACT

There is provided a process for enhancing the activity of a phenol oxidizing enzyme, comprising adding to the enzyme, as an enhancer for the activity of the enzyme, one or more compounds having the formula:

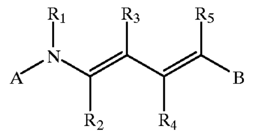

or

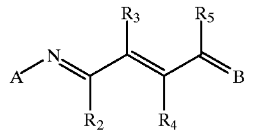

wherein:

A is an optionally substituted electron-withdrawing group, chosen from the group consisting of nitrile, carboxyl, and esters and salts thereof, amides, aldehydes, ketones, sulfoxides, sulfones, or sulphonates, and B is an optionally substituted electron-donating group, chosen from the group consisting of the oxide anion, sulfide anion, oxides, amines, imines, hydroxides, sulfides, ethers, carboxylic acids, and halogen substituents, and $R_1$–$R_5$ may each independently represent hydrogen, hydroxy, halogen, nitroso, formyl, carboxyl, and esters and salts thereof, carbamoyl, sulfo, and esters and salts hereof, sulfamoyl, nitro, amino, phenyl, $C_1$–$C_{20}$ alkyl, $C_1$–$C_8$ alkoxy, carbonyl-$C_1$–$C_6$-alkoxy, aryl-$C_1$–$C_6$-alkyl, and $R_2$ and $R_5$ together may form an alkylene group or an alkenylene group.

11 Claims, No Drawings

METHOD AND COMPOSITION FOR ENHANCING THE ACTIVITY OF AN ENZYME

TECHNICAL FIELD

The present invention generally relates to the activation of redox enzymes by means of enhancing agents. More in particular, the invention is concerned with the activation of phenol oxidizing enzymes, especially in a process for bleaching stains on fabrics during washing.

BACKGROUND AND PRIOR ART

Redox enzymes are enzymes which catalyze the transfer of electrons from an electron donor to an electron acceptor. In the case of phenol oxidizing enzymes, the electron donor is usually a phenolic compound and the electron acceptor is molecular oxygen or hydrogen peroxide, which is thereby reduced to $H_2O$. Phenol oxidizing enzymes are capable of using a wide variety of different phenolic compounds as electron donors, but they are very specific for molecular oxygen or hydrogen peroxide as the electron acceptor.

Examples of phenol oxidizing enzymes which use molecular oxygen as electron acceptor are laccases (EC 1.10.3.2), bilirubin oxidases (EC 1.3.3.5), mono phenol oxidizing enzymes (EC 1.14.18.1), catechol oxidases (EC 1.10.3.1). Phenol oxidizing enzymes which use hydrogen peroxide as electron acceptor are called peroxidases.

Phenol oxidizing enzymes can be utilised for a wide variety of applications, including the detergent industry, the paper and pulp industry (U.S. Pat. No. 4,690,895), the textile industry and the food industry. In the detergent industry, phenol oxidizing enzymes have been used for preventing the transfer of dyes in solution from one textile to another during detergent washing, an application commonly referred to as dye transfer inhibition.

For example, the use of peroxidases for bleaching fabrics during washing has been suggested in EP-A-424 398 (Novo Nordisk). WO-A-91/05839 (Novo Nordisk) describes the inhibition of dye transfer during the wash by means of peroxidase or an enzyme exhibiting oxidase activity on phenolic compounds. The compositions are said to bleach any dissolved textile dye so that no dye can redeposit upon the fabric.

It is also known that the activity of phenol oxidizing enzymes may be increased by the addition of certain organic compounds. The use of such activated enzyme systems for various purposes has also been described, for instance for inhibiting dye transfer in a washing process. The above mentioned WO-A-91/05839 (Novo Nordisk) describes that the addition of another oxidisable substrate may enhance the enzyme activity. Examples of such oxidisable substrates or "enhancers" are certain phenolic compounds, e.g. 2,4-dichlorophenol.

In three subsequent patent applications (WO-A-94/12619, WO-A-94/12620 and WO-A-94/12621, all Novo Nordisk) it is disclosed that the action of peroxidase in such anti dye-transfer compositions may be enhanced by the addition of a number of aromatic compounds, of which 2,2'-azo-bis-(3-ethylbenzo-thiazoline-6-sulphonate (ABTS) and Phenothiazine-10-propionate (PTP) appear to be the preferred compounds. WO-A-97/11217 (Novo Nordisk) discloses a process for bleaching stains by contacting the fabric in an aqueous medium with a phenol oxididizing enzyme and a "mediator", which is preferably of the phenotiazine-type.

However, some of these aromatic enhancer compounds may not be attractive as ingredients of detergent compositions for economical or environmental reasons. Furthermore, some of these enhancers like ABTS are, in their oxidized form, dyestuffs themselves. This has the disadvantage that the washed fabrics may be coloured by residual amounts of oxidised ABTS.

WO-A-97/06244 (Ciba) discloses various other compounds as enhancers for phenol oxidizing enzyme such as substituted naphtols, barbituric acids, and substituted coumarins.

Thus, although some of these approaches have been successful to a certain extent, there is still a need for alternative or improved enhancers for the activity of phenol oxidizing enzymes. In particular, there is a need for effective enzymatic bleach compositions, e.g. enzymatic bleaching detergent compositions. It is therefor an object of the present invention to provide such effective alternative or improved phenol oxidizing enzyme enhancers and enzymatic bleach compositions containing them.

We have now surprisingly found that these and other objects can be achieved by using certain N-containing compounds as phenol oxidizing enzyme enhancers.

DEFINITION OF THE INVENTION

According to a first aspect of the invention, there is provided a process for enhancing the activity of a phenol oxidizing enzyme, comprising adding to the enzyme, as an enhancer for the activity of said enzyme, one or more compounds having the formula:

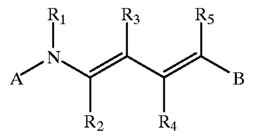

or

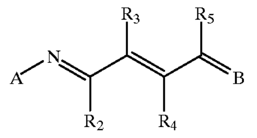

wherein:

A is an optionally substituted electron-withdrawing group, chosen from the group consisting of nitrile, carboxyl, and esters and salts thereof, amides, aldehydes, ketones, sulfoxides, sulfones, or sulphonates, and B is an optionally substituted electron-donating group, chosen from the group consisting of the oxide anion, sulfide anion, oxides, amines, imines, hydroxides, sulfides, ethers, carboxylic acids, and halogen substituents, and $R_1$–$R_5$ may each independently represent hydrogen, hydroxy, halogen, nitroso, formyl, carboxyl, and esters and salts thereof, carbamoyl, sulfo, and esters and salts hereof, sulfamoyl, nitro, amino, phenyl, $C_1$–$C_{20}$ alkyl, $C_1$–$C_8$ alkoxy, carbonyl-$C_1$–$C_6$-alkoxy, aryl-$C_1$–$C_6$-alkyl, and $R_2$ and $R_5$ together may form an alkylene group or an alkenylene group.

According to a second aspect, there is provided an enzymatic bleach composition comprising a phenol oxidizing enzyme and an enhancer, as shown above. According to a third aspect, there is provided a detergent composition comprising the enzymatic bleach composition and which additionally comprises one or more surfactants. According to a fourth aspect, there is provided a process for bleaching stains on fabrics.

DESCRIPTION OF THE INVENTION

A first aspect of the invention is a process for enhancing the activity of a phenol oxidizing enzyme by adding to the enzyme, certain specific compounds which are capable of enhancing the activity of said phenol oxidizing enzyme, the so-called "enhancers". A second aspect of the invention is formed by enzymatic bleach compositions comprising a phenol oxidizing enzyme and said enhancers.

(a) The Phenol Oxidizing Enzyme

The enzymatic bleach compositions according to the invention comprise, as a first constituent, a phenol oxidizing enzyme. A phenol oxidizing enzyme is defined for the purpose of the present invention as an enzyme or a system in which an enzyme, by using hydrogen peroxide or molecular oxygen, is capable of oxidising organic compounds containing phenolic groups. Examples of such enzymes are peroxidases and oxidases. Suitable enzymes are disclosed in EP-A-495 835 (Novo Nordisk). For instance, suitable peroxidases may be isolated from and are producible by plants or micro-organisms such as bacteria or fungi. Preferred fungi are strains belonging to the class of the Basidiomycetes, in particular Coprinus, or to the class of Hyphomycetes, in particular Arthromyces, especially *Arthromyces ramosus.* Other preferred sources are Hormographiella sp. or Soybean peroxidase. Other relevant peroxidases are haloperoxidases (U.S. Pat. No. 4,397,192) such as chloride peroxidases, bromide peroxidases and iodide peroxidases. Other potential sources of useful peroxidases are listed in B. C. Saunders et al., Peroxidases, London, 1964, pp 41–43.

In the context of this invention, phenol oxidizing enzymes which use oxygen as the oxidant, comprise any laccase comprised by the enzyme classification (EC 1.10.3.2), any catechol oxidase enzyme comprised by the enzyme classification (EC 1.10.3.1), any bilirubin oxidase enzyme comprised by the enzyme classification (EC 1.3.3.5) or any monophenol monooxygenase enzyme comprised by the enzyme classification (EC 1.14.99.1). The phenol oxidizing enzymes are known from microbial and plant origin. The microbial phenol oxidizing enzyme may be derived from bacteria or fungi (including filamentous fungi and yeasts) and suitable examples include a phenol oxidizing enzyme derivable from a strain of Aspergillus, Neurospora, e.g. *N. crasse,* Podospora, Botrytis, Collybia, Fomes, Lentinus, Pleurotus, Trametes, (previously called Polyporus), e.g. *T. villosa* and *T. versicolor,* Rhizoctonia, e.g. *R. solani,* Coprinus, e.g. *C. plicatilis* and *C. cinereus,* Psatyrella, Myceliophthora, e.g. *M. thermophylia,* Schytalidium, Phlebia, e.g. *P. radita* (WO-A-92/01046), Coriolus, e.g. *C. hirsutus* (JP-A-2-238885), Acremonium, e.g.*A. murorum,* or Stachybotrys, e.g. *Stachybotrys chartarum* or *Stachybotrys parvispora* (PCT/EP99/02042) (Unilever).

The phenol oxidizing enzyme may furthermore be one which is reproducible by a method comprising cultivating a host cell transformed with a recombinant DNA vector which carried a DNA sequence encoding said phenol oxidizing enzyme as well as DNA sequence encoding functions permitting the expression of the DNA sequence encoding phenol oxidizing enzyme, in a culture medium under conditions permitting the expression of the phenol oxidizing enzyme and the recovery of the phenol oxidizing enzyme from the culture.

Also of interest are synthetic or semi-synthetic derivatives and models of such enzymes, such as those comprising iron- or manganese-porphyrin systems, microperoxidases, and iron- or manganese-phthalocyanine compounds, e.g. as described in U.S. Pat. No. 4,077,768, WO-A-91/05858 and WO-A-92/16634.

(b) The Source of Hydrogen Peroxide

When a peroxidase is used in the enzymatic bleach compositions according to the invention, it is necessary to include a source of hydrogen peroxide. This may be hydrogen peroxide itself, but more stabilised forms of hydrogen peroxide such as perborate or percarbonate are preferred. Especially preferred is sodium percarbonate.

Alternatively, one may employ an enzymatic hydrogen peroxide-generating system. The enzymatic hydrogen peroxide-generating system may in principle be chosen from the various enzymatic hydrogen peroxide-generating systems, which have been disclosed in the art. For example, one may use an amine oxidase and an amine, an amino acid oxidase and an amino acid, cholesterol oxidase and cholesterol, uric acid oxidase and uric acid or a xanthine oxidase with xanthine. In the latter system, superoxide is generated which decomposes to give hydrogen peroxide. Preferably, however, the combination of a $C_1$–$C_4$ alkanol oxidase and a $C_1$–$C_4$ alkanol is used, and especially preferred is the combination of methanol oxidase and ethanol. The methanol oxidase is preferably isolated from a catalase-negative *Hansenula polymorpha* strain such as, for example, described in EP-A-244 920 (Unilever).

(c) The Enhancer

As further ingredient, the compositions of the invention comprise as an enhancer for the activity of said enzyme, one or more compounds having the formula:

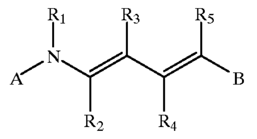

or

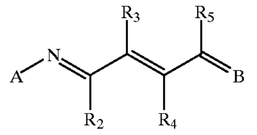

wherein:

A is an optionally substituted electron-withdrawing group (as desrcibed in J. March, 'Advanced Organic Chemistry, pg 17, 3d ed. (1985),, chosen from the group consisting of nitrile, carboxyl, and esters and salts thereof, amides, aldehydes, ketones, sulfoxides, sulfones, or sulphonates, and B is an electron-donating group, chosen from the group consisting of the oxide anion, sulfide anion, oxides, amines, imines, hydroxides, sulfides, ethers, carboxylic acids, and halogen substituents, and $R_1$–$R_5$ may each independently represent hydrogen, hydroxy, halogen, nitroso, formyl, carboxyl, and esters and salts thereof, carbamoyl, sulfo, and esters and salts hereof, sulfamoyl, nitro, amino, phenyl, $C_1$–$C_{20}$ alkyl, $C_1$–$C_8$ alkoxy, carbonyl-$C_1$–$C_6$-alkoxy, aryl-$C_1$–$C_6$-alkyl, and $R_2$ and $R_5$ together may form an alkylene group or an alkenylene group.

In the above drawing, no specific stereochemistry is implied. Furthermore, it should be noted that in the above formula, B may represent an —N—A or an =N—A group, in which case the structure would be symmetric.

Preferably, the carbamoyl, sulfamoyl and amino groups are further substituted once or twice with hydroxy, $C_1$–$C_6$-alkyl, $C_1$–$C_6$-alkoxy, in which the $C_1$–$C_6$-group may be saturated or unsaturated, branched or unbranched and may be substituted once or twice with halogen, nitroso, hydroxy, formyl, carboxy, and esters and salts thereof, carbamoyl, sulfo, and esters and salts thereof, sulfamoyl; and the phenyl group may be substituted with halogen, nitroso, hydroxy, formyl, carboxy, and esters and salts thereof, carbamoyl, sulfo, and esters and salts hereof, sulfamoyl; and the $C_1$–$C_{20}$ alkyl, $C_1$–$C_8$ alkoxy, carbonyl-$C_1$–$C_6$-alkoxy, and aryl-$C_1$–$C_6$-alkyl groups may be saturated or unsaturated, branched or unbranched, and may be substituted with halogen, hydroxy, nitroso, formyl, carboxy, and esters and salts thereof, carbamoyl, sulfo, and esters and salts thereof, sulfamoyl, nitro, amino, phenyl, aminoalkyl, piperidino, piperazinyl, pyrrolidin-2-yl, $C_1$–$C_6$-alkyl, $C_1$–$C_6$-alkoxy.

The preferred enhancers are phenyl-sulfonamides having the following formula:

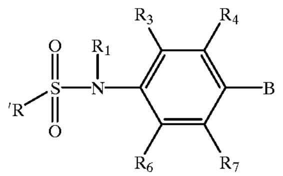

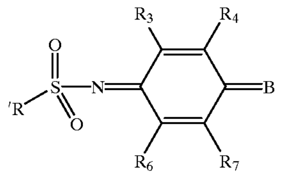

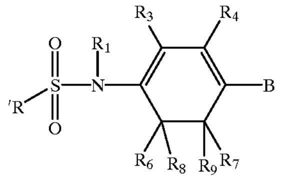

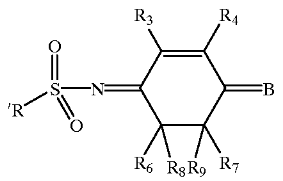

wherein R' represents an phenyl group, optionally substituted with 1–5 groups R", whereby R', R", $R_6$ and $R_7$ each may independently have the same meaning as $R_1$–$R_5$ above.

Much preferred are optionally substituted N-(4-hydroxyphenyl)-benzenesulfonamides. Especially preferred are halophenyl phenylsulphonamides, wherein B is an hydroxy or oxo group, and one or more of $R_3$, $R_4$, $R_6$ and $R_7$ are halogen.

Specific examples of the most preferred compounds include the following sulfonamides:

N-(2,3,5-tribromo-4-hydroxyphenyl)-benzenesulfonamide (further referred to as 3BrphenolBSA)

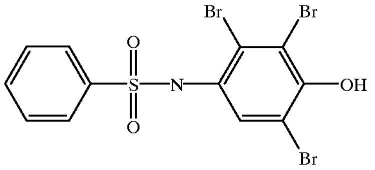

N-(2,3,5-tribromo-4-hydroxyphenyl) -4-Methyl benzenesulfonamide (further referred to as 3BrphenolMeBSA)

N-(2,3,5-trichloro-4-hydroxyphenyl)-benzenesulfonamide (further referred to as 3ClphenolBSA)

The above compounds can be prepared using standard organic synthesis techniques. More in particular, the bromo-benzenesulfonamides may be obtained by bromination of N-4-hydroxyphenyl phenylsulphonamide, as described by Toropin et al. in J. Org. Chem. USSR (Eng Transl.), 1986, p 894–899, and p 999–1005. The N-4-hydroxyphenyl phenylsulphonamide may be prepared by e.g. solid-phase synthesis, as described by Rajun & Kogan, Tetrahedron Lett. (1997), 38(19), 3373–3376.

(d) Applications

The process and the bleach composition of the present invention may in principle be applied in all situations where phenol oxidizing enzymes are now used or have been suggested for use, such as in fabric washing, pulp bleaching in the paper industry and waste water treatment. The invention is of particular use to formulate detergent compositions that are capable of bleaching stains on fabrics during washing, but also to formulate enzymatic anti dye-transfer compositions. The enzymatic bleach compositions and the detergent compositions of the invention may take any suitable physical form, such as a powder, an aqueous or non-aqueous liquid (which may be structured or isotropic), a paste, a gel or a tablet. However, granular detergents (powders) are preferred.

The enzymatic bleach compositions of the invention comprise about 0.001 to 50 mg of active enzyme per gram of detergent composition. Preferably, they comprise 0.001 to 5 mg of active enzyme protein per gram of detergent composition, more preferably 0.005 to 1.0 mg per gram. The phenol oxidizing enzymes used in the present invention can usefully be added to detergent compositions in any suitable form, i.e. the form of a granular composition, a liquid or a slurry of the enzyme, with carrier material (e.g. as in EP-A-258 068 and the Savinase (TM) and Lipolase (TM) products of Novo Nordisk), or a coating. A good way of adding the enzyme to a liquid detergent product is in the form of a slurry containing 0.5 to 50% by weight of the enzyme in a ethoxylated alcohol nonionic surfactant, such as described in EP-A-450 702 (Unilever).

If desired, a slow-release coating may be applied to the granulate of the phenol oxidizing enzyme. By means of such coatings, it is possible to achieve the controlled release of the enzyme when the granulate is introduced in the washing liquor. Preferred slow-release materials are compounds that are substantially insoluble in water. Examples of such materials include long-chain fatty acid mono, di-, triesters of glycerol, ethoxylated fatty alcohols, latexes, waxes, tallow, hydrogenation tallow, partially hydrolyzed tallow, hydrocarbons having a melting point in the range of 50–80° C.

(e) Surfactants

When used to formulate bleaching detergent compositions, the compositions of the invention will usually contain, one or more detergent-active compounds (surfactants) which may be chosen from soap and non-soap anionic, cationic, nonionic, amphoteric and zwitterionic detergent-active compounds, and mixtures thereof. Many suitable detergent-active compounds are available and are fully described in the literature, for example, in "Surface-Active Agents and Detergents", Volumes I and II, by Schwartz, Perry and Berch.

The preferred detergent-active compounds that can be used are soaps and synthetic non-soap anionic and nonionic compounds. Anionic surfactants are well-known to those skilled in the art. Examples include alkylbenzene sulphonates, particularly linear alkylbenzene sulphonates having an alkyl chain length of $C_8$–$C_{15}$; primary and secondary alkylsulphates, particularly $C_8$–$C_{15}$ primary alkyl sulphates; alkyl ether sulphates; olefin sulphonates; alkyl xylene sulphonates; dialkyl sulpho-succinates; and fatty acid ester sulphonates. Sodium salts are generally preferred. It was generally found to be advantageous to also include cationic surfactants into the composition. Examples of suitable cationic surfactants are given in WO-A-97/03160 and WO-A-98/17767 (Procter&Gamble).

Nonionic surfactants that may be used include the primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_{15}$ primary and secondary aliphatic alcohols ethoxylated with an average of from 1 to 10 (and preferably 3 to 7) moles of ethylene oxide per mole of alcohol. Non-ethoxylated nonionic surfactants include alkylpolyglycosides, glycerol monoethers, and polyhydroxyamides (glucamide). If the detergent composition comprises both nonionic and anionic surfactants, it is preferred that the ratio of nonionic surfactant to anionic surfactant is at least 1 to 3, more preferably at least 1 to 1.

The choice of detergent-active compound (surfactant), and the amount present, will depend on the intended use of the detergent composition. In fabric washing compositions, different surfactant systems may be chosen, as is well known to the skilled formulator, for handwashing products and for products intended for use in different types of washing machine.

The total amount of surfactant present will also depend on the intended end use and may be as high as 60% by weight, for example, in a composition for washing fabrics by hand. In compositions for machine washing of fabrics, an amount of from 5 to 40% by weight is generally appropriate. Detergent compositions suitable for use in most automatic fabric washing machines generally contain anionic non-soap surfactant, or nonionic surfactant, or combinations of the two in any ratio, optionally together with soap.

(f) Detergency Builders

The enzymatic bleach compositions of the invention will generally also contain one or more detergency builders. This detergency builder may be any material capable of reducing the level of free calcium ions in the wash liquor and will preferably provide the composition with other beneficial properties such as the generation of an alkaline pH, the suspension of soil removed from the fabric and the suspension of the fabric-softening clay material. The total amount of detergency builder in the compositions will suitably range from 5 to 80%, preferably from 10 to 60% by weight.

Inorganic builders that may be present include sodium carbonate, if desired in combination with a crystallisation seed for calcium carbonate, as disclosed in GB-A-1 437 950 (Unilever); crystalline and amorphous aluminosilicates, for example, zeolites as disclosed in GB-A-1 473 201 (Henkel), amorphous aluminosilicates as disclosed in GB-A-1 473 202 (Henkel) and mixed crystalline/amorphous aluminosilicates as disclosed in GB-A-1 470 250 (Procter & Gamble); and layered silicates as disclosed in EP-B-164 (Hacksawed). Inorganic phosphate builders, for example, sodium orthophosphate, pyrophosphate and tripolyphosphate, may also be present, but on environmental grounds those are no longer preferred.

The detergent compositions of the invention preferably contain an alkali metal, preferably sodium, aluminosilicate builder. Sodium aluminosilicates may generally be incorporated in amounts of from 10 to 70% by weight (anhydrous basis), preferably from 25 to 50% by weight. The alkali metal aluminosilicate may be either crystalline or amorphous or mixtures thereof, having the general formula:

$$0.8\text{–}1.5\ Na_2O.Al_2O_3.0.8\text{–}6\ SiO_2$$

These materials contain some bound water and are required to have a calcium ion exchange capacity of at least 50 mg CaO/g. The preferred sodium aluminosilicates contain 1.5–3.5 $Sio_2$ units (in the formula above). Both the amorphous and the crystalline materials can be prepared readily by reaction between sodium silicate and sodium aluminate, as amply described in the literature. Suitable crystalline sodium aluminosilicate ion-exchange detergency builders are described, for example, in GB-A-1 429 143 (Proctor & Gamble). The preferred sodium aluminosilicates of this type are the well-known commercially available zeolites A and X, and mixtures thereof. The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP-A-384 070 (Unilever). Zeolite MAP is defined as an alkali metal aluminosilicate of the zeolite P type having a silicon to aluminium ratio not exceeding 1.33, preferably within the range of from 0.90 to 1.33, and more preferably within the range of from 0.90 to 1.20. Especially preferred is zeolite MAP having a silicon to aluminium ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono-, di- and trisuccinates, carboxymethyloxysuccinates, carboxymethyloxymalonates, dipicolinates, hydroxyethyl-iminodiacetates, alkyl- and alkenylmalonates and succinates; and sulphonated fatty acid salts.

Especially preferred organic builders are citrates, suitably used in amounts of from 5 to 30% by weight, preferably from 10 to 25% by weight, and acrylic polymers, more especially acrylic/maleic copolymers, suitably used in amounts of from 0.5 to 15%, preferably from 1 to 10% by weight. Builders, both inorganic and organic, are preferably present in the form of their alkali metal salt, especially their sodium salt.

g. Bleach Components

Detergent compositions according to the invention may addtionally contain a conventional bleach system. Fabric washing compositions may desirably contain peroxy bleach compounds, for example, inorganic persalts or organic peroxyacids, capable of yielding hydrogen peroxide in aqueous solution.

Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate. Especially preferred is sodium percarbonate having a protective coating against destabilisation by moisture. Sodium percarbonate having a protective coating comprising sodium metaborate and sodium silicate is disclosed in GB-A-2 123 044 (Kao). The peroxy bleach compound is suitably present in an amount of from 5 to 35 wt %, preferably from 10 to 25 wt %.

The bleach system may contain apart from the hydrogen peroxide source, as disclosed above, also a peracid-forming bleach activator or precursor to improve bleaching action at low wash temperatures. Preferred bleach precursors are peroxycarboxylic acid precursors, more especially peracetic acid precursors and peroxybenzoic acid precursors; and peroxycarbonic acid precursors. Of special interest or bleach activators such as tetraacetylethylenediamine (TAED) or N,N-phthaloylaminoperoxy caproic acid (PAP). The novel quaternary ammonium and phosphonium bleach precursors disclosed in U.S. Pat. Nos. 4,751,015 and 4,818,426 (Lever Brothers Company) and EP-A-402 971 (Unilever) are also of great interest. Alternatively, peroxycarbonic acid precursors, in particular cholyl-4-sulphophenyl carbonate can be used. Also of interest are peroxybenzoic acid precursors, in particular, N,N,N-trimethylammonium toluoyloxy benzene sulphonate; and the cationic bleach precursors disclosed in EP-A-284 292 and EP-A-303 520 (Kao). The bleach precursor is suitably present in an amount of from 1 to 8 wt %, preferably from 2 to 5 wt %.

Alternatively, inorganic peroxyacids like potassium monopersulphate (MPS) may be employed. Alkyl hydroperoxides are another class of peroxy bleaching compounds. Examples of these materials include t-butyl hydroperoxide and cumene hydroperoxide.

Optionally, bleach catalysts can be included. Such compounds are well known in the art and include, for example, manganese-based catalysts as disclosed in U.S. Pat. Nos. 5 246 621, 5,244,594, 5,194,416, 5,114,606, EP-A-458 397 and EP-A-458 398 EP-A-509 787 or the iron-based catalysts as disclosed in WO-A-95/34628.

A bleach stabiliser (heavy metal sequestrant) may also be present. Suitable bleach stabilisers include ethylenediamine tetraacetate (EDTA) and the polyphosphonates such as Dequest (Trade Mark), EDTMP.

h. Additional Enzymes

The detergent compositions of the present invention may additionally comprise one or more enzymes, which provide cleaning performance, fabric care and/or sanitation benefits.

Said enzymes include oxidoreductases, transferases, hydrolases, lyases, isomerases and ligases. Suitable members of these enzyme classes are described in Enzyme nomenclature 1992: recommendations of the Nomenclature Committee of the International Union of Biochemistry and Molecular Biology on the nomenclature and classification of enzymes, 1992, ISBN 0-12-227165-3, Academic Press. The most recent information on the nomenclature of enzymes is available on the Internet through the ExPASy WWW server (http://www.expasy.ch/).

Examples of the hydrolases are carboxylic ester hydrolase, thiolester hydrolase, phosphoric monoester hydrolase, and phosphoric diester hydrolase which act on the ester bond; glycosidase which acts on O-glycosyl compounds; glycosylase hydrolysing N-glycosyl compounds; thioether hydrolase which acts on the ether bond; and exopeptidases and endopeptidases which act on the peptide bond. Preferable among them are carboxylic ester hydrolase, glycosidase and exo- and endopeptidases. Specific examples of suitable hydrolases include (1) exopeptidases such as aminopeptidase and carboxypeptidase A and B and endopeptidases such as pepsin, pepsin B, chymosin, trypsin, chymotrypsin, elastase, enteropeptidase, cathepsin B, papain, chymopapain, ficain, thrombin, plasmin, renin, subtilisin, aspergillopepsin, collagenase, clostripain, kallikrein, gastricsin, cathepsin D, bromelain, chymotrypsin C, urokinase, cucumisin, oryzin, proteinase K, thermomycolin, thermitase, lactocepin, thermolysin, bacillolysin. Preferred among them is subtilisin; (2) glycosidases such as α-amylase, β-amylase, glucoamylase, isoamylase, cellulase, endo-1,3(4)-β-glucanase (β-glucanase), xylanase, dextranase, polygalacturonase (pectinase), lysozyme, invertase, hyaluronidase, pullulanase, neopullulanase, chitinase, arabinosidase, exocellobiohydrolase, hexosaminidase, mycodextranase, endo-1,4-β-mannanase (hemicellulase), xyloglucanase, endo-β-galactosidase (keratanase), mannanase and other saccharide gum degrading enzymes as described in WO-A-99/09127. Preferred among them are α-amylase and cellulase; (3) carboxylic ester hydrolase including carboxylesterase, lipase, phospholipase, pectinesterase, cholesterol esterase, chlorophyllase, tannase and wax-ester hydrolase. Preferred among them is lipase.

Examples of transferases and ligases are glutathione S-transferase and acid-thiol ligase as described in WO-A-98/59028 and xyloglycan endotransglycosylase as described in WO-A-98/38288.

Examples of lyases are hyaluronate lyase, pectate lyase, chondroitinase, pectin lyase, alginase II. Especially preferred is pectolyase, which is a mixture of pectinase and pectin lyase.

A process for enhancing the efficacy of the bleaching action of oxidoreductases is by targeting them to stains by using antibodies or antibody fragments as described in WO-A-98/56885. Antibodies can also be added to control enzyme activity as described in WO-A-98/06812.

A preferred combination is a detergent composition comprising of a mixture of conventional detergent enzymes such as protease, amylase, lipase, cutinase and/or cellulase together with one or more plant cell wall degrading enzymes.

Endopeptidases (proteolytic enzymes or proteases) of various qualities and origins and having activity in various pH ranges of from 4–12 are available and can be used in the instant invention. Examples of suitable proteolytic enzymes are the subtilisins, which can be obtained from particular strains of *B. subtilis, B. lentus, B. amyloliquefaciens* and *B. licheniformis,* such as the commercially available subtilisins Savinase™, Alcalase™, Relase™, Kannase™ and Everlase™ as supplied by Novo Industri A/S, Copenhagen, Denmark or Purafect™, PurafectOxP™ and Properase™ as supplied by Genencor International. Chemically or genetically modified variants of these enzymes are included such as described in WO-A-99/02632 pages 12 to 16 and in WO-A-99/20727 and also variants with reduced allergenicity as described in WO-A-99/00489 and WO-A-99/49056.

Suitable lipases include those of bacterial or fungal origin as described in WO-A-99/11770 pages 33,34, such as the commercially available Lipolase™, Lipolase Ultra™, LipoPrime™, from Novo Nordisk, or Lipomax™ from Genencor. Chemically or genetically modified variants of these enzymes are included.

Suitable amylases include those of bacterial or fungal origin. Chemically or genetically modified variants of these enzymes are included as described in WO-A-99/02632 pages 18,19. Commercial cellulase are sold under the tradename Purastar™, Purastar OxAm™ (formerly Purafact Ox Am™) by Genencor; Termamyl™, Fungamyl™ and Duramyl™, all available from Novo Nordisk A/S.

Suitable cellulases include those of bacterial or fungal origin. Chemically or genetically modified variants of these enzymes are included as described in WO-A-99/02632 page 17. Particularly useful cellulases are the endoglucanases such as the EGIII from *Trichoderma longibrachiatum* as described in WO-A-94/21801 and the E5 from *Thermomonospora fusca* as described in WO-A-97/20025. Endoglucanases may consist of a catalytic domain and a cellulose binding domain or a catalytic domain only. Preferred cellulolytic enzymes are sold under the tradename Carezyme™, Celluzyme™ and Endolase™ by Novo Nordisk A/S; Puradax™ is sold by Genencor and KAC™ is sold by Kao corporation, Japan.

Detergent enzymes are usually incorporated in an amount of 0.00001% to 2%, and more preferably 0.001% to 0.5%, and even more preferably 0.01% to 0.2% in terms of pure enzyme protein by weight of the composition. Detergent enzymes are commonly employed in the form of granules made of crude enzyme alone or in combination with other components in the detergent composition. Granules of crude enzyme are used in such an amount that the pure enzyme is 0.001 to 50 weight percent in the granules. The granules are used in an amount of 0.002 to 20 and preferably 0.1 to 3 weight percent. Granular forms of detergent enzymes are known as Enzoguard™ granules, prills, marumes or T-granules. Granules can be formulated so as to contain an enzyme protecting agent (e.g. oxidation scavengers) and/or a dissolution retardant material. Other suitable forms of enzymes are liquid forms such as the "L" type liquids from Novo Nordisk, slurries of enzymes in nonionic surfactants such as the "SL" type sold by Novo Nordisk and microencapsulated enzymes marketed by Novo Nordisk under the tradename "LDP" and "CC".

The enzymes can be added as separate single ingredients (prills, granulates, stabilised liquids, etc. containing one enzyme) or as mixtures of two or more enzymes (e.g. cogranulates). Enzymes in liquid detergents can be stabilised by various techniques as for example disclosed in U.S. Pat. Nos. 4,261,868 and 4,318,818.

The detergent compositions of the present invention may additionally comprise one or more biologically active peptides such as swollenin proteins, expansins, bacteriocins and peptides capable of binding to stains.

i. Other Ingredients

The compositions of the invention may contain alkali metal, preferably sodium, carbonate, in order to increase detergency and ease processing. Sodium carbonate may suitably be present in amounts ranging from 1 to 60 wt %, preferably from 2 to 40 wt %. However, compositions containing little or no sodium carbonate are also within the scope of the invention.

Powder flow may be improved by the incorporation of a small amount of a powder structurant, for example, a fatty acid (or fatty acid soap), a sugar, an acrylate or acrylate/maleate polymer, or sodium silicate. One preferred powder structurant is fatty acid soap, suitably present in an amount of from 1 to 5 wt %.

The detergent compositions according to the present invention may also comprise from 0.001% to 10%, more preferably from 0.01% to 2%, more preferably from 0.05% to 1% by weight of polymeric dye transfer inhibiting agents. Said polymeric dye transfer inhibiting agents are normally incorporated into detergent compositions in order to inhibit the transfer of dyes from colored fabrics onto fabrics washed therewith. These polymers have the ability to complex or adsorb the fugitive dyes washed out of dyed fabrics before the dyes have the opportunity to become attached to other articles in the wash. Especially suitable polymeric dye transfer inhibiting agents are polyamine N-oxide polymers, copolymers of Nvinylpyrrolidone and N-vinylimidazole, polyvinylpyrrolidone polymers, polyvinyloxazolidones and polyvinylimidazoles or mixtures thereof.

Soil release agents useful in compositions of the present invention are conventionally copolymers or terpolymers of terephthalic acid with ethylene glycol and/or propylene glycol units in various arrangements. Examples of such polymers are disclosed in the commonly assigned U.S. Pat. Nos. 4,116,885 and 4,711,730 and EP-A-272 033.

Other materials that may be present in detergent compositions of the invention include sodium silicate; antiredeposition agents such as cellulosic polymers; inorganic salts such as sodium sulphate, lather control agents or lather boosters as appropriate, enzyme stabilizers, corrosion inhibitors, dyes, coloured speckles, perfumes, suds depressants, germicides, anti-tarnishing agents, opacifiers, optical brighteners, foam controllers, and fabric softening compounds. This list is not intended to be exhaustive.

Detergent compositions of the invention may be prepared by any suitable method. Particulate detergent compositions are suitably prepared by spray-drying a slurry of compatible heat-insensitive ingredients, and then spraying on or post-dosing those ingredients unsuitable for processing via the slurry. The skilled detergent formulator will have no difficulty in deciding which ingredients should be included in the slurry and which should not.

Particulate detergent compositions of the invention preferably have a bulk density of at least 400 g/l, more preferably at least 500 g/l. Such powders may be prepared either by post-tower densification of spray-dried powder, or by wholly non-tower methods such as dry mixing and granulation; in both cases a high-speed mixer/granulator may advantageously be used. Processes using high-speed mixer/granulators are disclosed, for example, in EP-A-340 013, EP-A-367 339, EP-A-390 251 and EP-A-420 317 (Unilever).

The invention will now be further illustrated in the following non-limiting Examples.

EXAMPLE 1

Bleaching of Tomato Stains

The potential of the various enhancer to boost the bleach performance of phenol oxidizing enzyme was assessed by washing cotton swatches soiled with tomato stains. Two different bleach monitors were used:

- Tomato extract material was prepared by acetone extraction of the chromophores from concentrated tomato paste. For the preparation of the stains, the colored acetone solution was applied to cotton swatches.
- Oily tomato stains were prepared by applying heated concentrated tomato paste, to which 5 wt % Soya oil was added, to cotton swatches.

The experiments were performed in small 80 ml containers, to which 15 ml of wash solution were added (indicated in tables). The pH of the wash solution was set to pH 9. Purified phenol oxidizing enzyme from *Acremonium murorum* was added to the wash solution at 20 mg/l. The enzyme from *Acremonium murorum* is decribed in WO-A-00/05349 (Unilever). The enhancers were all dosed at 250 $\mu$M. The wash solution was 50 mM Tris buffer.

The swatches were washed during 30 minutes, at 30° C. After the wash, the swatches were tumble-dried and the reflectance spectra were measured using a Minolta spectrometer. The color differences between the swatch before and after the wash data were expressed in the CIELAB L*a*b* color space. In this color space, L* indicates lightness and a* and b* are the chromaticity coordinates. Color differences between two swatches are expressed as ΔE, which is calculated from the following equation:

$$\Delta E=\sqrt{\Delta L^2+\Delta a^2+\Delta b^2}$$

The results are shown in Table 1 below:

Table 1: Stain bleach performance of the phenol oxidizing enzyme/enhancer system on tomato stains in the presence of different enhancers. A 50 mM Tris buffer solution was used as the wash solution.

| | Stain Monitor | | | |
|---|---|---|---|---|
| | Tomato Extract | | Oily Tomato Stain | |
| Enhancer | Without enzyme | With enzyme | Without enzyme | With enzyme |
| 3BrphenolBSA | 10.33 | 19.97 | 4.18 | 5.62 |
| 3Brphenol3MeBSA | 10.86 | 19.59 | 1.56 | 6.21 |

As can be seen from the ΔE values, the bleaching of the tomato stain is improved in the presence of the phenol enzyme/enhancer system.

EXAMPLE 2

Example 1 was repeated, using this time as wash solution a detergent formulation having the composition shown below, at a concentration of 2 g/l. The amounts are given in weight %.

| | |
|---|---|
| Linear Alkylbenzene Sulphonate | 24.0 |
| Sodium tripolyphosphate | 14.5 |
| Soda ash | 17.5 |
| Sodium silicate | 8.0 |
| SCMC | 0.37% |
| Blue pigment | 0.02% |
| Moisture/salts | ad 100 |

The results are shown in Table below:

Table 2: Stain bleach performance of the phenol oxidizing enzyme/enhancer system on tomato stains in the presence of different enhancers.

| | Stain Monitor | | | |
|---|---|---|---|---|
| | Tomato Extract | | Oily Tomato Stain | |
| Enhancer | Without enzyme | With enzyme | Without enzyme | With enzyme |
| 3BrphenolBSA | 12.99 | 26.87 | 6.89 | 10.95 |
| 3Brphenol3MeBSA | 12.86 | 27.57 | 6.87 | 11.71 |

It is apparent from the ΔE values that the bleaching of the tomato stain is improved in the presence of the phenol oxidizing enzyme/enhancer system. Furthermore, the improvement is more pronounced using the detergent formulation than using 50 mM Tris buffer as wash solution.

What is claimed is:

1. An enzymatic bleach composition comprising:

(a) a phenol oxidizing enzyme;

(b) an enhancer having a formula selected from the group consisting of:

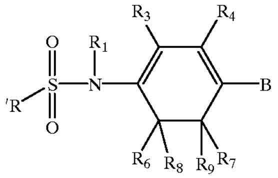

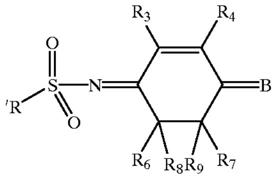

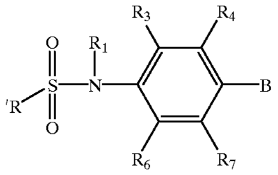

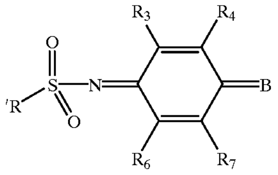

wherein

'R represents a phenyl group, optionally substituted with 1–5 groups R", whereby 'R, R", $R_1$, $R_3$, $R_4$ and $R_6$–$R_9$ each may independently represent: hydrogen, hydroxy, halogen, nitroso, formyl, carboxyl, and esters and salts thereof, carbamoyl, sulfo, and esters and salts hereof, sulfamoyl, nitro, amino, phenyl, $C_1$–$C_{20}$ alkyl, $C_1$–$C_8$ alkoxy, carbonyl-$C_1$–$C_6$-alkoxy, aryl-$C_1$–$C_6$-alkyl, and B is an optionally substituted electron-donating group, chosen from the group consisting of the oxide anion, sulfide anion, oxides, amines, imines, hydroxides, sulfides, ethers, carboxylic acids, and halogen substituents.

2. An enzymatic bleach composition according to claim 1, comprising (a) an enzyme exhibiting peroxidase activity and a source of hydrogen peroxide.

3. An enzymatic bleach composition according to claim 2, wherein the source of hydrogen peroxide is an alkali metal percarbonate.

4. An enzymatic bleach composition according to claim 2, wherein the amount of hydrogen peroxide is from 0.001 to 10 mM.

5. An enzymatic bleach composition according to claim 1, further comprising a surfactant.

6. A bleaching detergent composition according to claim 1, further comprising a proteolytic enzyme.

7. A bleaching detergent composition according to claim 1, further comprising a subtilisin protease.

8. A bleaching detergent composition according to claim 1, in the form of an granular detergent composition.

9. Process for removing coloured stains from fabrics in a washing process comprising contacting the stained fabric, in an aqueous medium, with a bleaching composition according to claim 1.

10. An enzymatic bleach composition according to claim 3 wherein the alkali metal percabonate is sodium percarbonate.

11. An enzymatic bleach composition according to claim 1 wherein the amount of hydrogen peroxide is from 0.005 to 1 mM.

* * * * *